United States Patent
Hsieh (10) Patent No.: US 6,408,042 B1
(45) Date of Patent: Jun. 18, 2002

(54) METHODS AND APPARATUS FOR CONE BEAM ARTIFACT SUPPRESSION IN SCANNING IMAGING SYSTEMS

(75) Inventor: Jiang Hsieh, Brookfield, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 09/882,160

(22) Filed: Jun. 15, 2001

(51) Int. Cl.⁷ ................................................ A61B 6/00
(52) U.S. Cl. ............................ 378/4; 378/19; 378/901
(58) Field of Search ........................ 378/4, 15, 19, 378/21, 901

(56) References Cited

U.S. PATENT DOCUMENTS

| | | |
|---|---|---|
| 5,396,528 A | 3/1995 | Hu et al. |
| 5,416,815 A | 5/1995 | Hsieh |
| 5,515,409 A * | 5/1996 | Hsieh .......................... 378/15 |
| 5,610,964 A * | 3/1997 | Flohr et al. ................... 378/15 |
| 5,727,041 A | 3/1998 | Hsieh |
| 5,812,628 A | 9/1998 | Hsieh |
| 6,035,012 A | 3/2000 | Hsieh |
| 6,061,419 A | 5/2000 | Hsieh et al. |
| 6,155,487 A | 9/2000 | Toth et al. |
| 6,134,292 A * | 10/2000 | Hsieh .......................... 378/19 |
| 6,215,841 B1 | 4/2001 | Hsieh |
| 6,233,308 B1 | 5/2001 | Hsieh |

FOREIGN PATENT DOCUMENTS

| | | |
|---|---|---|
| DE | 100 43 725 A 1 | 4/2001 |
| EP | 1 104 917 A2 | 6/2001 |

OTHER PUBLICATIONS

U. S. application No. 09/810,925, filed Mar. 16, 2001.

* cited by examiner

Primary Examiner—David V. Bruce
Assistant Examiner—Pamela R. Hobden
(74) Attorney, Agent, or Firm—Carl B. Horton, Esq.; Armstrong Teasdale LLP (57) ABSTRACT

One embodiment is a method for reconstructing at least one image representative of an object utilizing a scanning imaging system having a multislice detector array and a radiation source. The method includes helically scanning the object with the scanning imaging system to acquire a plurality of projection views of the object, including projection views acquired at different cone angles of the radiation beam; selecting a region of reconstruction (ROR) to define sets of conjugate samples in the projection views; and reconstructing at least one image of the object. The reconstruction includes weighting the sets of conjugate samples using a cone-angle dependent weighting function, and filtering and backprojecting the weighted samples.

32 Claims, 2 Drawing Sheets

METHODS AND APPARATUS FOR CONE BEAM ARTIFACT SUPPRESSION IN SCANNING IMAGING SYSTEMS

BACKGROUND OF THE INVENTION

This invention relates generally to methods and apparatus for radiation imaging systems and, more particularly, to methods and apparatus for combating cone beam artifacts utilizing weighted generalized helical interpolation.

In multislice computed tomographic (CT) imaging systems, a detector array is segmented so that a plurality of parallel or quasi-parallel slices of projection data are acquired and processed to construct a plurality of images corresponding to several slices though a volume. A range of pitches exists for which measurements are available at least at two source locations. Measurements acquired at different source positions are known as "conjugate measurements." Pitches for which conjugate measurements are available are known as "High Quality" (HQ) pitches. When an HQ pitch is used, a CT imaging system (or "scanner") is said to operate in "HQ mode." For a four-slice scanner, the helical pitch of the HQ mode is 3:1. An eight-slice scanner enables higher pitch modes to be used. A natural pitch selection for an eight-slice scanner is thus in the range of 5:1 to 7:1, to increase the volume coverage of a patient or object being imaged. However, because of increased cone-beam artifacts, it is difficult to maintain image quality when using higher pitch modes with known reconstruction methods and apparatus.

BRIEF SUMMARY OF THE INVENTION

There is therefore provided, in one aspect of the present invention, a method for reconstructing at least one image representative of an object with a scanning imaging system having a multislice detector array and a radiation source configured to emit a radiation beam through the object and towards the multislice detector array, the multislice detector array having a plurality of detector elements arranged in a plurality of detector rows. The method includes helically scanning the object with the scanning imaging system to acquire a plurality of projection views of the object, including projection views acquired at different cone angles of the radiation beam; selecting a region of reconstruction (ROR) to define sets of conjugate samples in the projection views; and reconstructing at least one image of the object, the reconstruction including weighting the sets of conjugate samples using a cone-angle dependent weighting function, and filtering and backprojecting the weighted samples.

In another aspect, the invention provides a method that includes helically scanning the object with the scanning imaging system to acquire a plurality of projection views of the object, including projecting views acquired at different cone angles of the radiation beam, selecting an ROR to define sets of conjugate samples in the projection views; and reconstructing at least one image of the object, the reconstruction including weighting the sets of conjugate samples using a cone-angle dependent weighting function, and filtering and backprojecting the weighted samples, the weighting including applying a detector row k dependent scaling factor $w_k$ that scales linearly and inversely with the cone angles.

In yet another aspect, the present invention provides a scanning imaging system for reconstructing at least one image representative of an object, the scanning imaging system including a multislice detector array, a radiation source configured to emit a radiation beam through an object to be imaged and towards the multislice detector array, the multislice detector array having a plurality of detector elements arranged in a plurality of detector rows. The scanning imaging system is configured to: helically scan the object to be imaged to acquire a plurality of projection views of the object, including projection views acquired at different cone angles of the radiation beam; select an ROR to define sets of conjugate samples in the projection views; and reconstruct at least one image of the object, wherein to reconstruct the at least one image, the multislice imaging system is configured to weight the sets of conjugate samples using a cone-angle dependent weighting function, and to filter and backproject the weighted samples.

In still another aspect, the present invention provides a scanning imaging system for reconstructing at least one image representative of an object, the scanning imaging system including a multislice detector array, a radiation source configured to emit a radiation beam through an object to be imaged and towards the multislice detector array, the multislice detector array having a plurality of detector elements arranged in a plurality of detector rows. The scanning imaging system is configured to; helically scan the object to be imaged to acquire a plurality of projection views of the object, including projection views acquired at different cone angles of the radiation beam; select an ROR to define sets of conjugate samples in the projection views; and reconstruct at least one image of the object, wherein to reconstruct the at least one image, the multislice imaging system is configured to weight the sets of conjugate samples using a cone-angle dependent weighting function, and to filter and backproject the weighted samples, wherein to weight the conjugate samples, the scanning imaging system is configured to apply a detector row k dependent scaling factor $w_k$ that scales linearly and inversely with said cone angles.

In another aspect, the present invention provides a processor for reconstructing at least one image representative of an object helically scanned by a scanning imaging system. The processor is configured to: input a plurality of projection views of a scanned object, including projection views acquired at different cone angles of a radiation beam by a multislice detector array having a plurality of detector rows; select an ROR to define sets of conjugate samples in the projection views; and reconstruct at least one image of the object, wherein to reconstruct the at least one image, the processor is configured to weight the sets of conjugate samples using a cone-angle dependent weighting function, and to filter and backproject the weighted samples.

In yet another aspect, the present invention provides a processor for reconstructing at least one image representative of an object helically scanned by a scanning imaging system. The processor is configured to: input a plurality of projection views of a scanned object, including projection views acquired at different cone angles of a radiation beam by a multislice detector array having a plurality of detector rows; select an ROR to define sets of conjugate samples in the projection views; and reconstruct at least one image of the object, wherein to reconstruct the at least one image, the processor is configured to weight the sets of conjugate samples using a cone-angle dependent weighting function, and to filter and backproject the weighted samples, wherein to weight the sets of conjugate samples, the processor is configured to apply a detector row k dependent scaling factor $w_k$ that scales linearly and inversely with the cone angles.

In still another aspect, the present invention provides a computer readable medium having encoded thereon instructions interpretable by a computer to instruct the computer to: input a plurality of projection views of a scanned object, including projection views acquired at different cone angles of a radiation beam by a multislice detector array having a plurality of detector rows; select an ROR to define sets of conjugate samples in the projection views; and reconstruct at least one image of the object, wherein to reconstruct the at least one image, the process is configured to weight the sets of conjugate samples using a cone-angle dependent weighting function, and to filter and backproject the weighted samples.

In still another aspect, the present invention provides a computer readable medium having encoded thereon instructions interpretable by a computer to instruct the computer to: input a plurality of projection views of a scanned object, including projection views acquired at different cone angles of a radiation beam by a multislice detector array having a plurality of detector rows; select an ROR to define sets of conjugate samples in the projection views; and reconstruct at least one image of the object, wherein to reconstruct the at least one image, the process is configured to weight the sets of conjugate samples using a cone-angle dependent weighting function, and to filter and backproject the weighted samples, wherein to instruct the computer to weight the sets of conjugate samples, the computer-readable medium has encoded thereon instructions configured to instruct the computer to apply a detector row k dependent scaling factor $w_k$ that scales linearly and inversely with the cone angles.

The above-described embodiments of the present invention reduce cone-beam artifacts in reconstructed images, thus providing increased imaging coverage while maintaining high image quality.

DETAILED DESCRIPTION OF THE INVENTION

Figure 1:
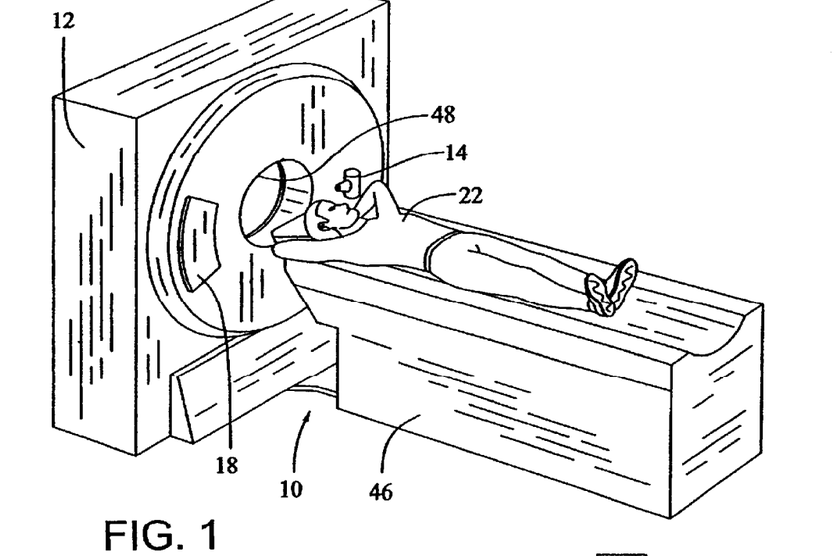
FIG. 1 is a pictorial view of a CT imaging system.
Figure 2:
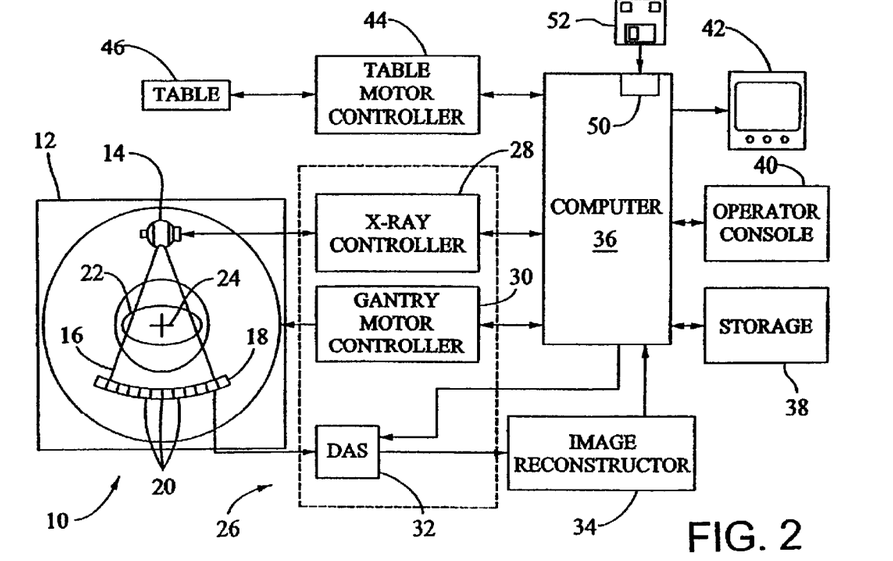
FIG. 2 is a block schematic diagram of the system illustrated in FIG. 1.

Referring to FIGS. 1 and 2, a scanning imaging system, for example, computed tomography (CT) imaging system 10, is shown as including a gantry 12 representative of a "third generation" CT imaging system. Gantry 12 has an x-ray source 14 that projects a beam of x-rays 16 toward a detector array 18 on the opposite side of gantry 12. Detector array 18 is formed by detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. FIG. 2 shows only a single row of detector elements 20 (i.e., a detector row). However, a multislice detector array 18 includes a plurality of parallel detector rows of detector elements 20 so that projection data corresponding to a plurality of parallel slices are, or can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48. In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown).

Figure 3:
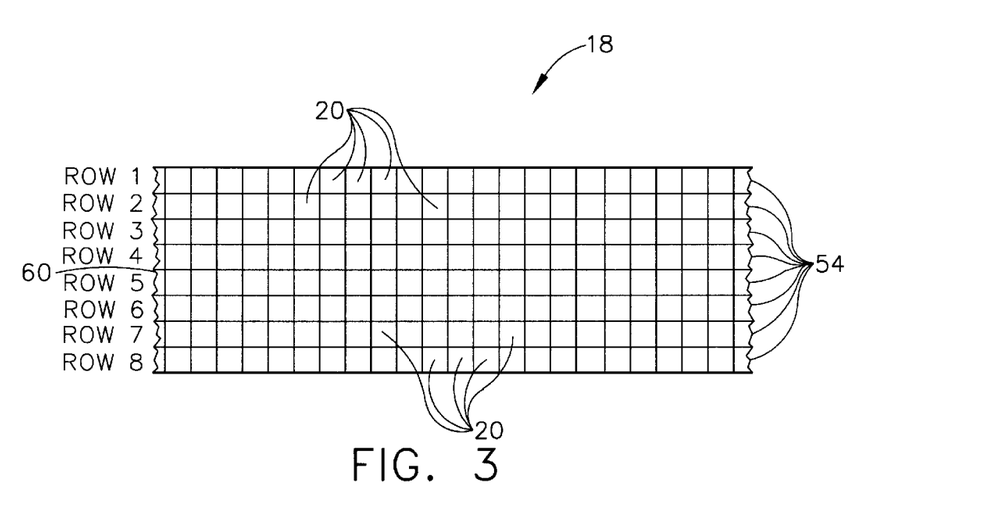
FIG. 3 is a simplified representation of a portion of an eight-slice detector array.
Figure 4:
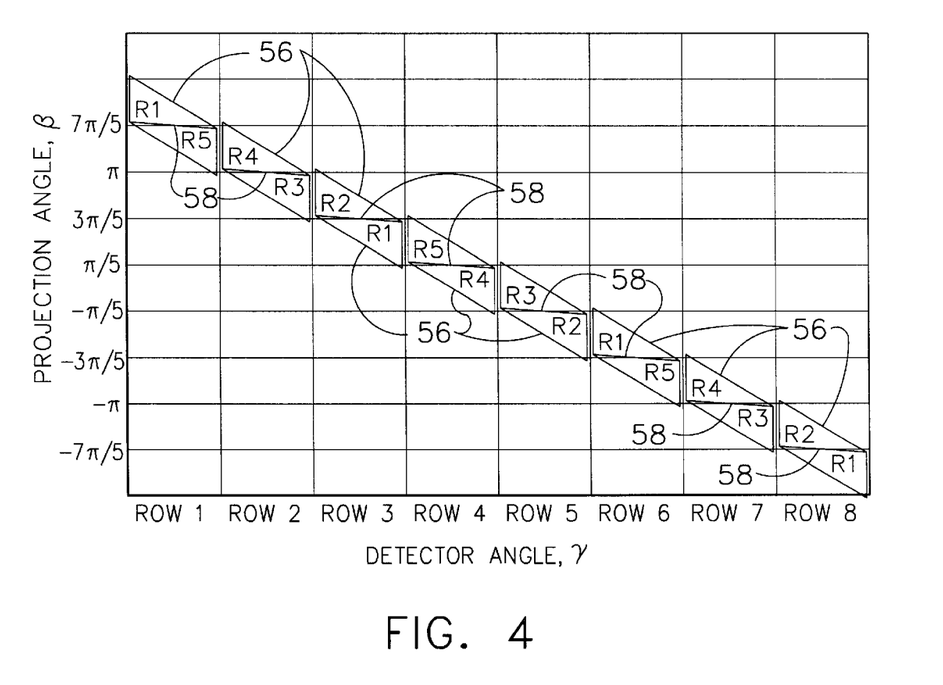
FIG. 4 is a graph showing representations of conjugate regions of a 5:1 pitch configuration for an eight slice imaging system of a type shown in FIGS. 1 and 2 that utilizes the detector array of FIG. 3.

In one embodiment and referring to FIG. 3, detector array 18 comprises eight detector rows 54 and is thus referred to as an eight-slice detector array. A representation of the sampling pattern of an eight-slice detector array at 5:1 helical pitch is shown in FIG. 4. A region of reconstruction (ROR) is a straight line in sinogram space written:

$$\beta_{0,k}(\gamma, \beta) = \frac{(9 - 2k)\pi}{5} - \alpha\gamma,$$

where k is a row number 1, 2, . . . ; β is a projection angle; γ is a detector angle; and α is a slope adjustment parameter.

Sampling regions 56 are labeled to indicate conjugate sampling regions. For example, sampling regions 56 labeled "R1" (for detector rows 1, 3, 6, and 8) form conjugate samples. Other than region R1, sampling regions 56 labeled R2, R3, R4, and R5 each contain only three conjugate regions. ROR 58 is represented by lines 58 between sampling regions 56 for each detector row in FIG. 4. If ROR 58 were independent of detector angle γ, it would be possible to ignore one of the conjugate regions 56 labeled R1 to ensure equal numbers of conjugate samples. It would also be possible to assign a weight of one-third to each conjugate region to ensure that the weights of the three regions sum to unity. However, the selection of ROR using the relationship written $\beta_{0,k}(\gamma,\beta)$ is channel dependent. If one of the conjugate regions were ignored by assigning a weight of zero to the region, a discontinuity in γ would result at ROR. Tomographic reconstruction theory indicates that the discontinuity in weighting function would cause severe image artifacts.

To avoid discontinuity, in one embodiment of the present invention, weights are selected to be identical for two regions belonging to the same detector row. For example, weights for regions 56 labeled R1 and R2 for detector row 8 are the same. A single weight $w_k$ is assigned for each detector row 54, where k is the detector row number. In an embodiment having eight detector rows, k=1, . . . , 8.

Weights are selected to satisfy the constraint that the summation of the weights for conjugate regions 56 equals unity:

$$\begin{cases} w_1 + w_3 + w_6 + w_8 = 1 \\ w_3 + w_5 + w_8 = 1 \\ w_2 + w_5 + w_7 = 1 \\ w_2 + w_4 + w_7 = 1 \\ w_1 + w_4 + w_6 = 1 \end{cases}$$

It is clear from the above relationships that there are an infinite number of weighting solutions, because the number of equations (five) is less than the number of weights (eight). As a result, in one embodiment of the present invention, an additional constraint is placed on the weights $w_k$, namely, that weights $w_k$ scale inversely to the cone angle. Weights for detector rows with a small cone angle are larger than weights for detector rows with a larger cone angle. For an eight-row detector array 18, detector row 4 and 5 straddle zero cone angle plane 60 (shown as a line between detector rows 4 and 5 in FIG. 3) and have the smallest cone angle. Rows 1 and 8 have the largest cone angle. In one embodiment, detector rows 54 that are symmetrical about zero cone angle plane 60 carry the same weight. Thus, $w_1=w_8$, $w_2=w_7$, $w_3=w_6$, and $w_4=w_5$ for an embodiment utilizing an eight-slice detector array 18. With these additional constraints:

$$\begin{cases} w_4 = 0.5 \\ w_2 = 0.25 \\ w_1 + w_3 = 0.5 \end{cases}$$

There are many ways of assigning weights to $w_1$ and $w_3$, each of which correspond to different embodiments of the present invention. For example, in one embodiment, weights are assigned that reduce linearly with the cone beam effect. Because the cone beam angle for detector row 3 is three times the cone angle for detector row 1, in this embodiment, $w_1=0.125$ and $w_3=0.375$. Other choices correspond to other embodiments.

A helical weighting function is applied. The helical weighting function is written as:

$$h_k(\gamma, \beta) = \begin{cases} \frac{w_k[\beta - \beta_{1,k}(\gamma, \beta)]}{\beta_{0,k}(\gamma, \beta) - \beta_{1,k}(\gamma, \beta)}, & \beta_{1,k}(\gamma, \beta) \le \beta < \beta_{0,k}(\gamma, \beta) \\ \frac{w_k[\beta_{2,k}(\gamma, \beta) - \beta]}{\beta_{2,k}(\gamma, \beta) - \beta_{0,k}(\gamma, \beta)}, & \beta_{0,k}(\gamma, \beta) \le \beta < \beta_{2,k}(\gamma, \beta) \\ 0, & \text{otherwise} \end{cases} \quad (4)$$

where:

$$\beta_{0,k}(\gamma, \beta) = \frac{(9-2k)\pi}{5} - \alpha\gamma;\ \beta_{1,k}(\gamma, \beta) = \frac{(8-2k)\pi}{5} + (\alpha - 2)\gamma;$$

$$\beta_{2,k}(\gamma, \beta) = \frac{(10-2k)\pi}{5} + (\alpha - 2)\gamma;$$

and $w_k$ is a row-dependent scaling factor and equals 0.125, 0.25, 0.375, 0.5, 0.5, 0.375, 0.25, and 0.125 for $k=1, \ldots, 8$.

In another embodiment, the a nonlinear helical interpolation is used. Also in one embodiment, the ROR is not a straight line in the sinogram space, but rather is defined in a piecewise linear or in a nonlinear fashion.

In one embodiment of the present invention, images of an object are constructed by scanning an object 22 with an scanning imaging system (for example, CT imaging system 10) having a multislice detector array 18 and a radiation source 14 configured to emit a radiation beam 16 through the object and towards multislice detector array 18. Multislice detector array 18 has a plurality of detector elements 20 arranged in a plurality of detector rows 54. To produce images of object 22, object 22 is helically scanned with scanning imaging system 10 to acquire a plurality of projection views of object 22, including projection views acquired at different cone angles of radiation beam 16. An ROR is selected to define sets of conjugate samples (i.e., sampling regions 56) in the projection views. An image of object 52 is reconstructed by weighting the sets of conjugate samples utilizing a cone-angle dependent weighting function and by filtering and backprojecting the weighted samples. In one embodiment, the weighting of conjugate samples 56 includes applying a detector row k dependent scaling factor $w_k$ that scales inversely to the cone angles of detector rows 54. In one embodiment, selecting of a region of reconstruction includes selecting a straight line in a sonogram space, the straight line described by an equation written as:

$$\beta_{0,k}(\gamma, \beta) = \frac{(9-2k)\pi}{5} - \alpha\gamma,$$

where k is a row number 1, 2, ...; $\beta$ is a projection angle; $\gamma$ is a detector angle; and $\alpha$ is a slope adjustment parameter.

In one embodiment, the ROR is selected as a piecewise linear ROR. In another embodiment, the ROR is selected as a nonlinear ROR. In yet another embodiment, weighting the sets of conjugate samples includes applying a detector row k dependent scaling factor $w_k$ that scales linearly and inversely with the cone angles. In still another embodiment, the scanning imaging system is a computed tomographic (CT) imaging system, the multislice detector array has eight detector rows, and wherein the cone-angle dependent weighting functions are written as:

$$h_k(\gamma, \beta) = \begin{cases} \frac{w_k[\beta - \beta_{1,k}(\gamma, \beta)]}{\beta_{0,k}(\gamma, \beta) - \beta_{1,k}(\gamma, \beta)}, & \beta_{1,k}(\gamma, \beta) \le \beta \le \beta_{0,k}(\gamma, \beta) \\ \frac{w_k[\beta_{2,k}(\gamma, \beta) - \beta]}{\beta_{2,k}(\gamma, \beta) - \beta_{0,k}(\gamma, \beta)}, & \beta_{0,k}(\gamma, \beta) \le \beta \le \beta_{2,k}(\gamma, \beta) \\ 0, \text{otherwise,} \end{cases}$$

where:

$$\beta_{0,k}(\gamma, \beta) = \frac{(9-2k)\pi}{5} - \alpha\gamma;\ \beta_{1,k}(\gamma, \beta) = \frac{(8-2k)\pi}{5} + (\alpha - 2)\gamma;$$

$$\beta_{2,k}(\gamma, \beta) = \frac{(10-2k)\pi}{5} + (\alpha - 2)\gamma\ \text{for}\ k = 1, \ldots, 8;\ \text{and}$$

$$w_k = \begin{cases} 0.125, & k=1 \\ 0.25, & k=2 \\ 0.375, & k=3 \\ 0.5, & k=4 \\ 0.5, & k=5 \\ 0.375, & k=6 \\ 0.25, & k=7 \\ 0.125, & k=8. \end{cases}$$

In one embodiment, helically scanning the object comprises scanning the object at a helical pitch of 5:1.

Other embodiments of the present invention include apparatus described above as scanning imaging system 10. The imaging system is configured to perform one or more of the methods described above using, for example, image reconstructor 34 to receive sampled and digitized projection views and computer 36 which stores the image in a mass storage device 38. An associated cathode ray tube display 42 allows the operator to observe the reconstructed image. In one embodiment, firmware and/or software is configured to instruct either or both of image reconstructor 34 and/or computer 36 to control imaging system 10 to perform one or more of the method embodiments described above.

It is possible to reconstruct images of an object 22 after scanning (e.g., at a later date), on a processor 36 separate from imaging system 10. Some of these embodiments are similar to the scanning imaging system embodiments described above, but differ in that hardware, software and/or firmware is not necessarily provided to perform a helical scan to collect projection data. In one embodiment, a processor comprises at least a computer 36, which may be, but is not necessarily part of imaging system 10. The processor may also comprise a separate image reconstructor 34. The processor is configured to accept as input a plurality of projection views of a scanned object. The projection views include projection views acquired at different cone angles of a radiation beam by a multislice detector array having a plurality of detector rows. The processor is configured to select a region of reconstruction to define sets of conjugate samples in the projection views, and to reconstruct at least one image of the object. To reconstruct the image, the processor is configured to weight sets of conjugate samples using a cone-angle dependent weighting function, and to filter and backproject the weighted samples. In yet another embodiment, a computer readable medium (e.g., a floppy disk or a CD-ROM) is provided that has instructions interpretable by a computer or processor 36 to instruct it to perform these steps.

Embodiments of the present invention provide increased coverage while maintaining high image quality. In particular, at least one embodiment of the present invention produces high quality images from projection views acquired from an eight-slice detector array at a pitch of 5:1.

As used herein, an element or step recited in the singular and preceded with the word "a" or "an" should be understood as not excluding plural said elements or steps, unless such exclusion is explicitly recited. Furthermore, passages referring to "one embodiment" of the present invention are not intended to be interpreted as excluding the existence of additional embodiments that also incorporate the recited features.

While the invention has been described in terms of various specific embodiments, those skilled in the art will recognize that the invention can be practiced with modification within the spirit and scope of the claims.

What is claimed is:

1. A method for reconstructing at least one image representative of an object with a scanning imaging system having a multislice detector array and a radiation source configured to emit a radiation beam through the object and towards the multislice detector array, the multislice detector array having a plurality of detector elements arranged in a plurality of detector rows, said method comprising:
   helically scanning the object with the scanning imaging system to acquire a plurality of projection views of the object, including projection views acquired at different cone angles of the radiation beam;
   selecting a region of reconstruction (ROR) to define sets of conjugate samples in the projection views; and
   reconstructing at least one image of the object, said reconstruction including weighting the sets of conjugate samples using a cone-angle dependent weighting function, and filtering and backprojecting the weighted samples.

2. A method in accordance with claim 1 wherein said weighting the sets of conjugate samples includes applying a detector row k dependent scaling factor $w_k$ that scales inversely to the cone angles.

3. A method in accordance with claim 2 wherein said selecting a region of reconstruction comprises selecting a straight line in a sonogram space, the straight line written as:

$$\beta_{0,k}(\gamma, \beta) = \frac{(9-2k)\pi}{5} - \alpha\gamma,$$

where:
   k is a row number 1, 2, . . . ;
   β is a projection angle;
   γ is a detector angle; and
   α is a slope adjustment parameter.

4. A method in accordance with claim 1 wherein said selecting an ROR comprises selecting a piecewise linear ROR.

5. A method in accordance with claim 1 wherein said selecting an ROR comprises selecting a nonlinear ROR.

6. A method for reconstructing at least one image representative of an object with a scanning imaging system having a multislice detector array and a radiation source configured to emit a radiation beam through the object and towards the multislice detector array, the multislice detector array having a plurality of detector elements arranged in a plurality of detector rows, said method comprising:
   helically scanning the object with the scanning imaging system to acquire a plurality of projection views of the object, including projection views acquired at different cone angles of the radiation beam;
   selecting a region of reconstruction (ROR) to define sets of conjugate samples in the projection views; and
   reconstructing at least one image of the object, said reconstruction including weighting the sets of conjugate samples using a cone-angle dependent weighting function, and filtering and backprojecting the weighted samples;
   said weighting the sets of conjugate samples includes applying a detector row k dependent scaling factor $w_k$ that scales linearly and inversely with the cone angles.

7. A method in accordance with claim 6 wherein the scanning imaging system is a computed tomographic (CT) imaging system, the multislice detector array has eight detector rows, and wherein the cone-angle dependent weighting functions are written as:

$$h_k(\gamma, \beta) = \begin{cases} \frac{w_k[\beta - \beta_{1,k}(\gamma, \beta)]}{\beta_{0,k}(\gamma, \beta) - \beta_{1,k}(\gamma, \beta)}, & \beta_{1,k}(\gamma, \beta) \le \beta \le \beta_{0,k}(\gamma, \beta) \\ \frac{w_k[\beta_{2,k}(\gamma, \beta) - \beta]}{\beta_{2,k}(\gamma, \beta) - \beta_{0,k}(\gamma, \beta)}, & \beta_{0,k}(\gamma, \beta) \le \beta \le \beta_{2,k}(\gamma, \beta) \\ 0, & \text{otherwise,} \end{cases}$$

where:
   k is a row number 1, 2, . . . ;
   β is a projection angle;
   γ is a detector angle;

α is a slope adjustment parameter;

$$\beta_{0,k}(\gamma, \beta) = \frac{(9-2k)\pi}{5} - \alpha\gamma; \beta_{1,k}(\gamma, \beta) = \frac{(8-2k)\pi}{5} + (\alpha-2)\gamma; \text{ and}$$

$$\beta_{2,k}(\gamma, \beta) = \frac{(10-2k)\pi}{5} + (\alpha-2)\gamma \text{ for } k = 1, \ldots, 8; \text{ and}$$

$$w_k = \begin{cases} 0.125, & k=1 \\ 0.25, & k=2 \\ 0.375, & k=3 \\ 0.5, & k=4 \\ 0.5, & k=5 \\ 0.375, & k=6 \\ 0.25, & k=7 \\ 0.125, & k=8. \end{cases}$$

8. A method in accordance with claim 7 wherein said helical scanning of the object comprises scanning the object at a helical pitch of 5:1.

9. A scanning imaging system for reconstructing at least one image representative of an object, said scanning imaging system comprising a multislice detector array, a radiation source configured to emit a radiation beam through an object to be imaged and towards said multislice detector array, said multislice detector array comprising a plurality of detector elements arranged in a plurality of detector rows, said scanning imaging system configured to:

helically scan the object to be imaged to acquire a plurality of projection views of the object, including projection views acquired at different cone angles of said radiation beam;

select a region of reconstruction (ROR) to define sets of conjugate samples in said projection views; and reconstruct at least one image of the object, wherein to reconstruct said at least one image, said multislice imaging system is configured to weight said sets of conjugate samples using a cone-angle dependent weighting function, and to filter and backproject said weighted samples.

10. A scanning imaging system in accordance with claim 9 wherein to weight said sets of conjugate samples, said scanning imaging system is configured to apply a detector row k dependent scaling factor $w_k$ that scales inversely to said cone angles.

11. A scanning imaging system in accordance with claim 10 wherein to select a region of reconstruction, said scanning imaging system is configured to select a straight line in a sonogram space, said straight line written as:

$$\beta_{0,k}(\gamma, \beta) = \frac{(9-2k)\pi}{5} - \alpha\gamma,$$

where:

k is a row number 1, 2, . . . ;
β is a projection angle;
γ is a detector angle; and
α is a slope adjustment parameter.

12. A scanning imaging system in accordance with claim 9 wherein to select an ROR, said scanning imaging system is configured to select a piecewise linear ROR.

13. A scanning imaging system in accordance with claim 9 wherein to select an ROR, said scanning imaging system is configured to select a nonlinear ROR.

14. A scanning imaging system for reconstructing at least one image representative of an object, said scanning imaging system comprising a multislice detector array, a radiation source configured to emit a radiation beam through an object to be imaged and towards said multislice detector array, said multislice detector array comprising a plurality of detector elements arranged in a plurality of detector rows, said scanning imaging system configured to:

helically scan the object to be imaged to acquire a plurality of projection views of the object, including projection views acquired at different cone angles of said radiation beam;

select a region of reconstruction (ROR) to define sets of conjugate samples in said projection views; and reconstruct at least one image of the object, wherein to reconstruct said at least one image, said multislice imaging system is configured to weight said sets of conjugate samples using a cone-angle dependent weighting function, and to filter and backproject said weighted samples;

wherein to weight said sets of conjugate samples, said scanning imaging system is configured to apply a detector row k dependent scaling factor $w_k$ that scales linearly and inversely with said cone angles.

15. A scanning imaging system in accordance with claim 14 wherein said scanning imaging system is a computed tomographic (CT) imaging system, said multislice detector array has eight detector rows, and wherein said cone-angle dependent weighting functions are written as:

$$h_k(\gamma, \beta) = \begin{cases} \frac{w_k[\beta - \beta_{1,k}(\gamma, \beta)]}{\beta_{0,k}(\gamma, \beta) - \beta_{1,k}(\gamma, \beta)}, & \beta_{1,k}(\gamma, \beta) \le \beta \le \beta_{0,k}(\gamma, \beta) \\ \frac{w_k[\beta_{2,k}(\gamma, \beta) - \beta]}{\beta_{2,k}(\gamma, \beta) - \beta_{0,k}(\gamma, \beta)}, & \beta_{0,k}(\gamma, \beta) \le \beta \le \beta_{2,k}(\gamma, \beta) \\ 0, & \text{otherwise,} \end{cases}$$

where:

k is a row number 1, 2, . . . ;
β is a projection angle;
γ is a detector angle;
α is a slope adjustment parameter;

$$\beta_{0,k}(\gamma, \beta) = \frac{(9-2k)\pi}{5} - \alpha\gamma; \beta_{1,k}(\gamma, \beta) = \frac{(8-2k)\pi}{5} + (\alpha-2)\gamma; \text{ and}$$

$$\beta_{2,k}(\gamma, \beta) = \frac{(10-2k)\pi}{5} + (\alpha-2)\gamma \text{ for } k = 1, \ldots, 8; \text{ and}$$

$$w_k = \begin{cases} 0.125, & k=1 \\ 0.25, & k=2 \\ 0.375, & k=3 \\ 0.5, & k=4 \\ 0.5, & k=5 \\ 0.375, & k=6 \\ 0.25, & k=7 \\ 0.125, & k=8. \end{cases}$$

16. A scanning imaging system in accordance with claim 15 configured to helically scan the object at a helical pitch of 5:1.

17. A processor for reconstructing at least one image representative of an object helically scanned by a scanning imaging system, said processor configured to:

input a plurality of projection views of a scanned object, including projection views acquired at different cone angles of a radiation beam by a multislice detector array having a plurality of detector rows;

select a region of reconstruction (ROR) to define sets of conjugate samples in said projection views; and reconstruct at least one image of the object, wherein to reconstruct said at least one image, said processor is configured to weight said sets of conjugate samples using a cone-angle dependent weighting function, and to filter and backproject said weighted samples.

18. A processor in accordance with claim 17 wherein to weight said sets of conjugate samples, said processor is configured to apply a detector row k dependent scaling factor $w_k$ that scales inversely to the cone angles.

19. A processor in accordance with claim 18 wherein to select a region of reconstruction, said processor is configured to select a straight line in a sonogram space, said straight line written as:

$$\beta_{0,k}(\gamma, \beta) = \frac{(9 - 2k)\pi}{5} - \alpha\gamma,$$

where:

k is a row number 1, 2, . . . ;

β is a projection angle;

γ is a detector angle; and

α is a slope adjustment parameter.

20. A processor in accordance with claim 17 wherein to select an ROR, said scanning imaging system is configured to select a piecewise linear ROR.

21. A processor in accordance with claim 17 wherein to select an ROR, said scanning imaging system is configured to select a nonlinear ROR.

22. A processor for reconstructing at least one image representative of an object helically scanned by a scanning imaging system, said processor configured to:

input a plurality of projection views of a scanned object, including projection views acquired at different cone angles of a radiation beam by a multislice detector array having a plurality of detector rows;

select a region of reconstruction (ROR) to define sets of conjugate samples in said projection views; and reconstruct at least one image of the object, wherein to reconstruct said at least one image, said processor is configured to weight said sets of conjugate samples using a cone-angle dependent weighting function, and to filter and backproject said weighted samples;

wherein to weight said sets of conjugate samples, said processor is configured to apply a detector row k dependent scaling factor $w_k$ that scales linearly and inversely with the cone angles.

23. A processor in accordance with claim 22 wherein said cone-angle dependent weighting functions are written as:

$$h_k(\gamma, \beta) = \begin{cases} \frac{w_k[\beta - \beta_{1,k}(\gamma, \beta)]}{\beta_{0,k}(\gamma, \beta) - \beta_{1,k}(\gamma, \beta)}, & \beta_{1,k}(\gamma, \beta) \le \beta \le \beta_{0,k}(\gamma, \beta) \\ \frac{w_k[\beta_{2,k}(\gamma, \beta) - \beta]}{\beta_{2,k}(\gamma, \beta) - \beta_{0,k}(\gamma, \beta)}, & \beta_{0,k}(\gamma, \beta) \le \beta \le \beta_{2,k}(\gamma, \beta) \\ 0, & \text{otherwise,} \end{cases}$$

where:

k is a row number 1, 2, . . . ;

β is a projection angle;

γ is a detector angle;

α is a slope adjustment parameter;

$$\beta_{0,k}(\gamma, \beta) = \frac{(9 - 2k)\pi}{5} - \alpha\gamma; \beta_{1,k}(\gamma, \beta) = \frac{(8 - 2k)\pi}{5} + (\alpha - 2)\gamma; \text{ and}$$

$$\beta_{2,k}(\gamma, \beta) = \frac{(10 - 2k)\pi}{5} + (\alpha - 2)\gamma \text{ for } k = 1, \ldots, 8; \text{ and}$$

$$w_k = \begin{cases} 0.125, & k = 1 \\ 0.25, & k = 2 \\ 0.375, & k = 3 \\ 0.5, & k = 4 \\ 0.5, & k = 5 \\ 0.375, & k = 6 \\ 0.25, & k = 7 \\ 0.125, & k = 8. \end{cases}$$

24. A processor in accordance with claim 23 configured to input a plurality of projection views scanned at a helical pitch of 5:1.

25. A computer-readable medium having encoded thereon instructions interpretable by a computer to instruct the computer to:

input a plurality of projection views of a scanned object, including projection views acquired at different cone angles of a radiation beam by a multislice detector array having a plurality of detector rows;

select a region of reconstruction (ROR) to define sets of conjugate samples in said projection views; and reconstruct at least one image of the object, wherein to reconstruct said at least one image, said processor is configured to weight said sets of conjugate samples using a cone-angle dependent weighting function, and to filter and backproject said weighted samples.

26. A computer-readable medium in accordance with claim 25 wherein to instruct the computer to weight said sets of conjugate samples, said computer-readable medium has encoded thereon instructions configured to instruct the computer to apply a detector row k dependent scaling factor $w_k$ that scales inversely to the cone angles.

27. A computer-readable medium in accordance with claim 25 wherein to instruct the computer to select a region of reconstruction, said computer-readable medium has encoded thereon instructions configured to instruct the computer to select a straight line in a sonogram space, said straight line written as:

$$\beta_{0,k}(\gamma, \beta) = \frac{(9 - 2k)\pi}{5} - \alpha\gamma,$$

where:

k is a row number 1, 2, . . . ;

β is a projection angle;

γ is a detector angle; and

α is a slope adjustment parameter.

28. A computer-readable medium in accordance with claim 25 wherein instruct the computer to select an ROR, said computer-readable medium has encoded thereon instructions configured to instruct the computer to select a piecewise linear ROR.

29. A computer-readable medium in accordance with claim 25 wherein to instruct the computer to select an ROR, said computer-readable medium has encoded thereon instructions configured to instruct the computer to select a nonlinear ROR.

30. A computer-readable medium having encoded thereon instructions interpretable by a computer to instruct the computer to:

input a plurality of projection views of a scanned object, including projection views acquired at different cone angles of a radiation beam by a multislice detector array having a plurality of detector rows;

select a region of reconstruction (ROR) to define sets of conjugate samples in said projection views; and reconstruct at least one image of the object, wherein to reconstruct said at least one image, said processor is configured to weight said sets of conjugate samples using a cone-angle dependent weighting function, and to filter and backproject said weighted samples;

wherein to instruct the computer to weight said sets of conjugate samples, said computer-readable medium has encoded thereon instructions configured to instruct the computer to apply a detector row k dependent scaling factor $w_k$ that scales linearly and inversely with the cone angles.

31. A computer readable medium in accordance with claim 30 wherein said cone-angle dependent weighting functions are written as:

$$h_k(\gamma, \beta) = \begin{cases} \dfrac{w_k[\beta - \beta_{1,k}(\gamma, \beta)]}{\beta_{0,k}(\gamma, \beta) - \beta_{1,k}(\gamma, \beta)}, & \beta_{1,k}(\gamma, \beta) \le \beta \le \beta_{0,k}(\gamma, \beta) \\ \dfrac{w_k[\beta_{2,k}(\gamma, \beta) - \beta]}{\beta_{2,k}(\gamma, \beta) - \beta_{0,k}(\gamma, \beta)}, & \beta_{0,k}(\gamma, \beta) \le \beta \le \beta_{2,k}(\gamma, \beta) \\ 0, & \text{otherwise,} \end{cases}$$

where:

k is a row number 1, 2, . . . ;

β is a projection angle;

γ is a detector angle;

α is a slope adjustment parameter;

$$\beta_{0,k}(\gamma, \beta) = \frac{(9-2k)\pi}{5} - \alpha\gamma;\ \beta_{1,k}(\gamma, \beta) = \frac{(8-2k)\pi}{5} + (\alpha - 2)\gamma;\ \text{and}$$

$$\beta_{2,k}(\gamma, \beta) = \frac{(10-2k)\pi}{5} + (\alpha - 2)\gamma\ \text{for}\ k = 1, \ldots, 8;\ \text{and}$$

$$w_k = \begin{cases} 0.125, & k = 1 \\ 0.25, & k = 2 \\ 0.375, & k = 3 \\ 0.5, & k = 4 \\ 0.5, & k = 5 \\ 0.375, & k = 6 \\ 0.25, & k = 7 \\ 0.125, & k = 8. \end{cases}$$

32. A computer-readable medium in accordance with claim 31 having encoded thereon instructions configured to instruct the computer to input a plurality of projection views scanned at a helical pitch of 5:1.

\* \* \* \* \*

UNITED STATES PATENT AND TRADEMARK OFFICE
CERTIFICATE OF CORRECTION

PATENT NO.     : 6,408,042 B1
DATED          : June 18, 2002
INVENTOR(S)    : Hsieh It is certified that error appears in the above-identified patent and that said Letters Patent is hereby corrected as shown below:

<u>Column 12,</u>
Line 50, delete "wherein instruct" and insert therefor -- wherein to instruct --.

Signed and Sealed this

Twenty-eighth Day of January, 2003

JAMES E. ROGAN
*Director of the United States Patent and Trademark Office*